US009793579B2

(12) United States Patent
Zilbershlag (10) Patent No.: US 9,793,579 B2
(45) Date of Patent: Oct. 17, 2017

(54) BATTERIES FOR USE IN IMPLANTABLE MEDICAL DEVICES

(71) Applicant: Leviticus Cardio Ltd., Givat Shmuel (IL)

(72) Inventor: Michael Zilbershlag, Givat Shmuel (IL)

(73) Assignee: Leviticus Cardio Ltd., Givat Shmuel (IL)

( * ) Notice: Subject to any disclaimer, the term of this patent is extended or adjusted under 35 U.S.C. 154(b) by 525 days.

(21) Appl. No.: 14/535,528

(22) Filed: Nov. 7, 2014

(65) Prior Publication Data

US 2015/0130283 A1 May 14, 2015

Related U.S. Application Data

(60) Provisional application No. 61/901,751, filed on Nov. 8, 2013.

(51) Int. Cl.
| | |
|---|---|
| *H01M 10/42* | (2006.01) |
| *H01M 2/34* | (2006.01) |
| *H01M 10/44* | (2006.01) |
| *H01M 10/48* | (2006.01) |
| *A61N 1/378* | (2006.01) |
| *H01M 10/052* | (2010.01) |

(52) U.S. Cl.
CPC ........ *H01M 10/4257* (2013.01); *A61N 1/378* (2013.01); *H01M 2/34* (2013.01); *H01M 10/4207* (2013.01); *H01M 10/441* (2013.01); *H01M 10/482* (2013.01); *H01M 10/488* (2013.01); *H01M 10/052* (2013.01); *H01M 2010/4271* (2013.01); *H01M 2200/00* (2013.01); *Y10T 307/625* (2015.04)

(58) Field of Classification Search
CPC ....... H01M 10/052; H01M 2010/4271; H01M 2200/00; H01M 10/4257; Y10T 307/625; A61N 1/378
See application file for complete search history.

(56) References Cited

U.S. PATENT DOCUMENTS

| 4,143,661 A | 3/1979 | LaForge et al. |
|---|---|---|
| 4,665,896 A | 5/1987 | LaForge et al. |
| 4,906,229 A | 3/1990 | Wampler |
| (Continued) | | |

FOREIGN PATENT DOCUMENTS

| NO | 2007003351 A1 | 1/2007 |
|---|---|---|
| WO | 2013/085996 A1 | 6/2013 |

OTHER PUBLICATIONS

Farmer, J. et al., "Wireless Battery Management System for Safe High-Capacity Energy Storage," 31st Annual Battery Seminar (Orlando, FL), 2014, 4 pages.

(Continued)

*Primary Examiner* — Robert Deberadinis
(74) *Attorney, Agent, or Firm* — Brown Rudnick LLP (57) ABSTRACT

The present disclosure provides devices, systems, and methods for identifying conditions in a battery that predict fault or failure, alerting a user to the condition, and providing solutions to mitigate the potential harm that would otherwise result from the fault or failure. Further provided are battery casing designs for improved safety. These systems, devices, and methods are applicable to batteries generally, and are particularly useful in the field of implanted medical devices for mitigating the dangers of battery faults or explosions occurring within the body.

45 Claims, 11 Drawing Sheets

(56) References Cited

U.S. PATENT DOCUMENTS

| | | | |
|---|---|---|---|
| 4,957,504 | A | 9/1990 | Chardack |
| 5,089,017 | A | 2/1992 | Young et al. |
| 5,095,903 | A | 3/1992 | DeBellis |
| 5,507,629 | A | 4/1996 | Jarvik |
| 5,749,855 | A | 5/1998 | Reitan |
| 5,991,665 | A | 11/1999 | Wang et al. |
| 6,070,103 | A | 5/2000 | Ogden |
| 6,129,704 | A | 10/2000 | Forman et al. |
| 6,135,729 | A | 10/2000 | Aber |
| 6,280,377 | B1 | 8/2001 | Talpade |
| 6,421,889 | B1 | 7/2002 | Chien |
| 6,527,699 | B1 | 3/2003 | Goldowsky |
| 6,531,847 | B1 | 3/2003 | Tsukamoto et al. |
| 6,761,681 | B2 | 7/2004 | Schmid et al. |
| 6,772,011 | B2 | 8/2004 | Dolgin |
| 6,891,353 | B2 | 5/2005 | Tsukamoto et al. |
| 7,433,794 | B1 | 10/2008 | Berdichevsky et al. |
| 7,613,497 | B2 | 11/2009 | Govari et al. |
| 7,650,192 | B2 | 1/2010 | Wahlstrand |
| 7,738,965 | B2 | 6/2010 | Phillips et al. |
| 7,741,734 | B2 | 6/2010 | Joannopoulos et al. |
| 7,821,230 | B2 | 10/2010 | Studyvin et al. |
| 7,825,543 | B2 | 11/2010 | Karalis et al. |
| 7,825,629 | B2 | 11/2010 | Studyvin et al. |
| 7,825,776 | B2 | 11/2010 | Smith et al. |
| 7,928,691 | B2 | 4/2011 | Studyvin et al. |
| 7,956,725 | B2 | 6/2011 | Smith |
| 8,075,472 | B2 | 12/2011 | Zilbershlag et al. |
| 8,129,865 | B2 | 3/2012 | Krumme et al. |
| 8,244,367 | B2 | 8/2012 | Wahlstrand et al. |
| 8,278,784 | B2 | 10/2012 | Cook et al. |
| 8,285,388 | B2 | 10/2012 | Wahlstrand |
| 8,579,789 | B1 | 11/2013 | Zilbershlag |
| 8,585,572 | B2 | 11/2013 | Mehmanesh |
| 8,840,539 | B2 | 9/2014 | Zilbershlag |
| 8,845,510 | B2 | 9/2014 | Zilbershlag |
| 8,961,389 | B2 | 2/2015 | Zilbershlag |
| 8,979,728 | B2 | 3/2015 | Zilbershlag |
| 9,343,224 | B2 | 5/2016 | Zilbershlag |
| 2003/0163020 | A1 | 8/2003 | Frazier |
| 2004/0014315 | A1 | 1/2004 | Lai et al. |
| 2004/0054251 | A1 | 3/2004 | Liotta |
| 2004/0115038 | A1 | 6/2004 | Nuesser et al. |
| 2005/0220636 | A1 | 10/2005 | Henein et al. |
| 2006/0085039 | A1 | 4/2006 | Hastings et al. |
| 2006/0085041 | A1 | 4/2006 | Hastings et al. |
| 2007/0132587 | A1 | 6/2007 | Smith et al. |
| 2007/0182578 | A1 | 8/2007 | Smith |
| 2007/0255223 | A1 | 11/2007 | Phillips et al. |
| 2008/0041930 | A1 | 2/2008 | Smith et al. |
| 2008/0109054 | A1 | 5/2008 | Hastings et al. |
| 2008/0238680 | A1 | 10/2008 | Posamentier et al. |
| 2008/0292478 | A1 | 11/2008 | Baykut et al. |
| 2009/0243813 | A1 | 10/2009 | Smith et al. |
| 2010/0045114 | A1 | 2/2010 | Sample et al. |
| 2010/0052811 | A1 | 3/2010 | Smith et al. |
| 2010/0076247 | A1 | 3/2010 | Zilbershlag et al. |
| 2010/0081379 | A1 | 4/2010 | Cooper et al. |
| 2010/0187913 | A1 | 7/2010 | Smith et al. |
| 2010/0197994 | A1 | 8/2010 | Mehmanesh |
| 2011/0080051 | A1 | 4/2011 | Lee et al. |
| 2011/0193688 | A1 | 8/2011 | Forsell |
| 2011/0278948 | A1 | 11/2011 | Forsell |
| 2011/0301668 | A1 | 12/2011 | Forsell |
| 2012/0123284 | A1 | 5/2012 | Kheradvar |
| 2012/0146575 | A1 | 6/2012 | Armstrong et al. |
| 2012/0150291 | A1 | 6/2012 | Aber et al. |
| 2012/0235502 | A1 | 9/2012 | Kesler et al. |
| 2012/0239118 | A1 | 9/2012 | Ozawa et al. |
| 2013/0043736 | A1 | 2/2013 | Zilbershlag |
| 2013/0053624 | A1 | 2/2013 | Zilbershlag |
| 2013/0141109 | A1 | 6/2013 | Love et al. |
| 2014/0031607 | A1 | 1/2014 | Zilbershlag et al. |
| 2014/0163307 | A1 | 6/2014 | Zilbershlag |
| 2014/0236172 | A1 | 8/2014 | Hastings et al. |
| 2016/0023004 | A1 | 1/2016 | Forsell |

OTHER PUBLICATIONS

Dermott, J. & Bond, J., "Safety Considerations for Lithium-Ion Flight Batteries," Power Sources Conference, Orlando, Jun. 2014, 4 pages.

Garcia, H.E. et al., "On-line State-of-Health and Remaining-Useful-Life Assessment of Batteries using Rapid Impedance Spectrum Measurements," 45th Power Sources Symposium, Las Vegas, Abstract 7.3, 2012, 4 pages.

Patridge, C.J. & Love, C.T., "Impedance Spectroscopy Diagnostic for Monitoring Li-ion Batteries," 45th Power Sources Symposium, Las Vegas, Abstract 7.4, 2012, 4 pages.

Non Final Office Action mailed May 8, 2017 for U.S. Appl. No. 15/097,867 (17 Pages).

International Search Report Mailed Jan. 30, 2009 for International Application No. PCT/IL2008/000604 (4Pages).

BATTERIES FOR USE IN IMPLANTABLE MEDICAL DEVICES

CROSS-REFERENCE TO RELATED APPLICATION

This application claims the benefit of, and priority to, U.S. Provisional Patent Application No. 61/901,751, filed Nov. 8, 2013, the entire contents of which is incorporated herein by reference.

TECHNICAL FIELD

The present disclosure generally relates to the field of batteries and particularly to safety features of batteries for use with implantable medical devices such as wirelessly-powered ventricular assist devices (VADs).

BACKGROUND INFORMATION

A lithium-ion battery (LIB) is a type of rechargeable battery that is widely used in various applications due to its very high energy density compared to other rechargeable battery types. LIBs are commercially available in portable electronics, power tools, electric vehicles, and many other devices.

Commercially available LIBs are generally designed to be charged and discharged at room temperature. Such consumer-targeted LIBs also are designed to safely discharge down to a cut-off voltage of around 2.5-3.0 V.

It is known to use LIBs to power medical implants, such as ventricular assist devices (VADs). Unlike consumer-use LIBs, the LIBs used in medical implants are designed to be charged and discharged at body temperature (around 37° C.). Also, medical implant LIBs typically are designed to discharge down to close to 0 (zero) V. This low cut-off voltage capability for implantable LIBs is a safety feature to protect the LIBs from over-discharge conditions which can damage the LIB cell and lead to its failure.

Although commonly used, LIBs present certain safety hazards. LIBs are particularly susceptible to abuse, which can lead to thermal runaway. Abuse can be external physical abuse, such as puncture, compression, dropping, vibration, or exposure to heat or fire. Abuse can also result from internal causes like over-charging, over-discharging, high rate charge at low temperature, or high or low temperature operation.

Thermal runaway refers to a situation where an increase in temperature causes a further increase in temperature, leading to a dangerous chain reaction. In such conditions, temperatures may quickly rise to unsafe levels, creating a potentially destructive result such as an explosion or fire. Thermal runaway can result from an internal fault, either from improper use or raw material defects.

To prevent dangerous conditions and explosions, consumer LIBs generally have vents, which allow the cell to release excess internal pressure. In the event of an abusive situation, the vents can release vapors of the cell's organic solvent electrolyte. Unlike consumer LIBs, the LIB s for use in implantable medical devices are hermetically sealed and have no vents, due to the damage that would be done to the body if vapors or organic solvent electrolytes escaped from the cell.

For life-sustaining medical devices, battery failure could lead to catastrophic results. For any battery implanted in the body, a battery explosion could do significant harm to the user. Some batteries known in the art are capable of measuring temperature to determine that a fault has occurred. But for critical devices like VADs, once a fault has occurred, it may be too late to mitigate the disastrous health effects.

SUMMARY

What is needed is a system and method for monitoring a working multi-cell battery pack, such as a Lithium-ion battery pack, for parameters in a cell that predict a battery failure or explosion before it happens. Then a user could be alerted to the condition and respond to the situation to minimize or avoid the potential harm. Also needed are improved battery casings for use with implanted battery packs that would adequately respond to abuse without causing physical harm to the user.

The present disclosure provides devices, systems, and methods for identifying one or more conditions of a battery that could result in fault or failure of the battery, making adjustments to the configuration of the battery to mitigate the conditions, and alerting a user of the conditions. The disclosed devices, systems, and methods are particularly useful in the field of implanted medical devices. These devices, systems, and methods help prevent the risk associated with a battery fault or explosion occurring inside a patient's body. According to the invention, when a potential fault or failure in the battery is identified, an implanted medical device can be caused to continue operating with its battery in a safer configuration. Also the patient within which the device is implanted can be alerted about the fault or failure and instructed to switch to a backup external power source. The battery can also alert the user that it has met a certain threshold probability of explosion, and that the user should immediately schedule a surgery to replace it.

In some embodiments of the invention, a battery management system (BMS) or controller unit monitors the function of the battery, including the individual cells of a multi-cell battery. In response to potential fault conditions, the BMS makes adjustments to the configuration of the battery to allow it to continue functioning. In response to a fault condition in a multi-cell battery, for example, the BMS can turn off, isolate, or otherwise disable a problematic cell and boost the voltage of the remaining functional cells. In other embodiments, the BMS can turn on a backup or reserve cell by activating a shunt. The reserve cell can take the place of the debilitated cell and the BMS can rebalance the remaining cells to maintain proper voltage output of the battery as a whole. In some embodiments of the invention, the BMS can assess whether the faulty cell remains capable of providing at least enough voltage to run the auxiliary functions of the electronic device, and if so, the BMS can assign the diminished cell to power those functions.

The disclosure also provides methods and systems for warning a user that the battery has had a fault or will potentially have a fault in the future. The alert may include information about the condition of the battery, such as that it has exceeded a threshold of probability to stop working or to explode. The warning can serve to alert the user to secure some backup power source, or it can alert the user that surgery is required to replace the defective battery. In embodiments involving implantable electronic devices, the backup power source can be an external wired or wireless power source.

Also provided in the present disclosure are battery casing designs for use with implantable electronic devices that allow venting of the battery to prevent overheating or explosions, while protecting the user from severe bodily harm.

DETAILED DESCRIPTION

Various aspects, features, objects, and advantages of the disclosed innovations will become apparent through reference to the following description and the drawings. Any particular embodiments described herein are not mutually exclusive and can exist in various combinations and permutations even if not specifically indicated herein. Also, various modifications may be made to the embodiments described herein, and the disclosed embodiments and details should not be construed as limiting but instead as illustrative of some embodiments in accordance with the inventions.

A battery according to the present disclosure is capable of identifying a fault or a condition that is a precursor to a fault or that predicts a fault. The fault or pre-fault condition is identified based on the measurement of certain parameters in a cell or cells. Based on one or more measured parameters, the battery may determine that the battery has faulted, is likely to have a fault in the near future, or is experiencing some other error or potential error. The battery may detect that the likelihood of explosion has reached a certain threshold. In response, the battery may reconfigure itself to allow it to continue functioning. It may also trigger an alert, which notifies the user or some other person about the condition so that he or she can take steps to mitigate the potential harm. The alert may involve one or more of: notifying the user to the condition; notifying the user that the battery has reconfigured itself to continue functioning; notifying the user of the amount of time before a fault or explosion occurs; instructing a user that a replacement battery is or will be necessary; instructing the user to supply a backup wireless power source; or instructing the user to connect a wired power source.

The battery may predict a fault situation using inputs from the cells including but not limited to temperature, voltage, current, resistance, charge speed, discharge speed, electrolyte levels, corrosion, environmental conditions, or other measurable parameters known in the art. For example, a multi-cell battery may monitor the temperature of each cell. If a cell reaches a temperature above a certain threshold, but still below the level that would indicate a fault, the battery may respond to that condition by reconfiguring the battery to prevent the potential fault. It may also alert a user about the potential problem. In its reconfigured state, the battery may be able to continue operating at least long enough so that the user can respond to the alert by replacing or supplementing the battery with an external wireless or wired power source. In this way, catastrophic faults or failures can be avoided, as problems with the battery are addressed before they arise.

A battery of the present disclosure can detect conditions indicating that a cell is highly likely to fault (for example, when the probability of fault is greater than 10%, 25%, 50%, 75%, or 90%), and it can also detect conditions that indicate a fault is less likely to occur (for example, when the probability of fault is less than 1%, 0.1%, 0.01% or less). Depending on the severity of the condition and how likely the cell is to fault, the battery may respond in different ways, with different measures of mitigation and different levels of alerts to the user.

The battery response may also be related to the particular type of risk posed by the condition. For example, if the condition of a cell is such that it has a 0.0001% likelihood to explode, the response may be to immediately disconnect the cell and alert the patient to schedule a battery replacement surgery. On the other hand, if the condition of a cell is such that it has a 90% chance to stop working but less than a 0.0001% chance of exploding, the battery may simply reconfigure itself to continue working, but not send an urgent alert to the user about needing a replacement. Alternately, the battery in that situation could do nothing until the cell actually stopped working.

For implanted Lithium-ion batteries in particular, it is vital to avoid explosions and other failures. The present disclosure provides improvements to known batteries, which reduce the likelihood of explosions by notifying user's of dangerous conditions so that the battery can be replaced before the explosion occurs.

Figure 1:
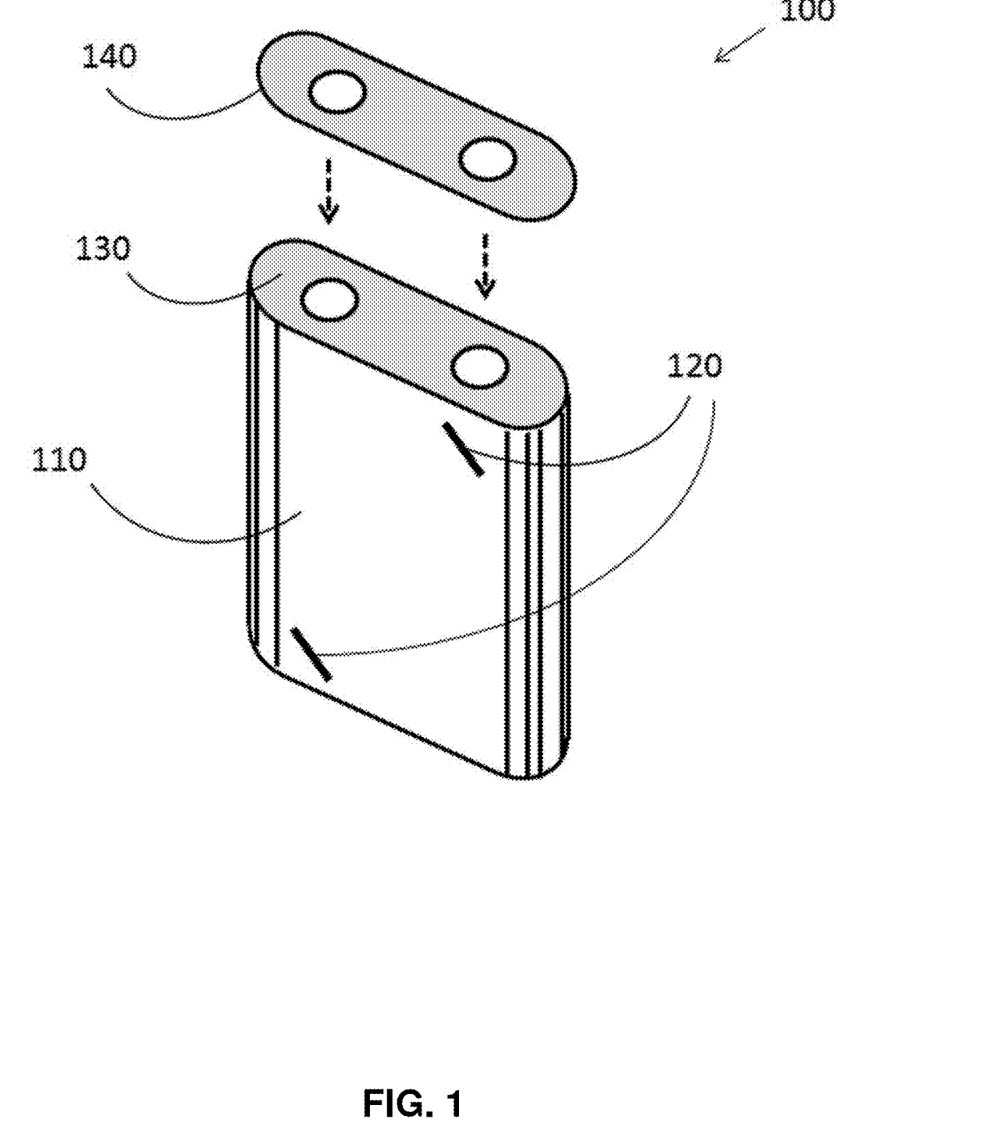
FIG. 1 shows a known rechargeable battery.

FIG. 1 shows an example of a known rechargeable battery 100. The battery casing 110 is typically made from aluminum or steel. The casing 110 has two vents 120 for built-in redundancy. The battery 100 has a current interrupt device 130 at the top of the cell, and a discrete positive temperature coefficient (PTC) device 140. The PTC device 140 is a resistor that increases resistance as battery temperature rises to prevent thermal runaway. In embodiments, a PTC device may be located inside or outside the cell case. It provides a current limiting function primarily for low-current applications, and it can reset itself when the over-current condition is corrected.

Figure 2:
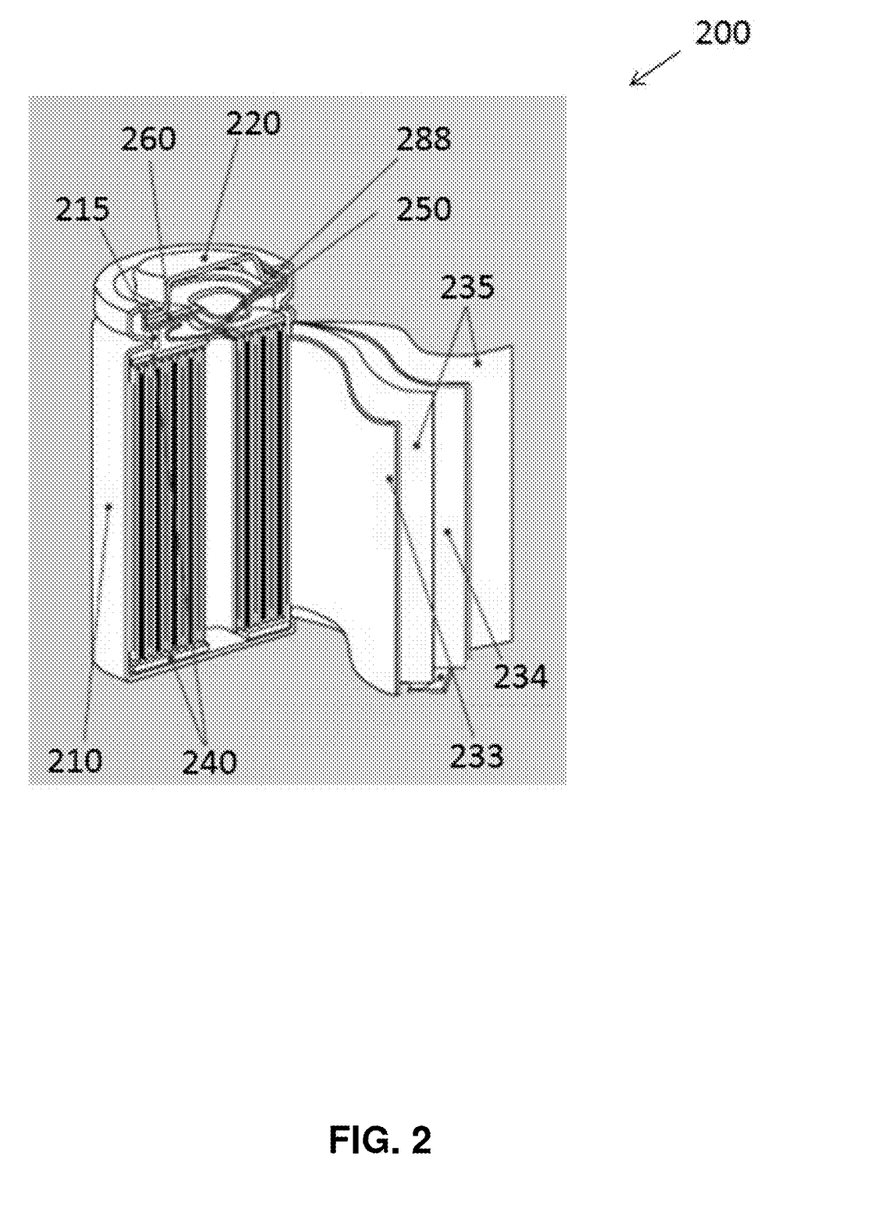
FIG. 2 shows a known lithium-ion battery.

FIG. 2 shows a known lithium-ion battery (LIB) 200, which embodies known safety features. The battery 200 comprises a casing 210 with a positive cap 220 connected with a gasket 215. The casing 210 surrounds cylindrical positive electrodes 233 and negative electrodes 234, with separators 235 in between. The battery 200 features insulation 240 to maintain cell temperature. The battery 200 also features a current interrupt device (CID) 250. If internal pressures get too high, the CID 250 electrically disconnects the cell. The CID 250 acts as a non-resetting circuit breaker. It may comprise a safety valve, an insulating spacer, and a thin metal plate that connects to the electrodes in the cell. When gasses build within the cell, the safety valve deforms, thereby causing it to separate from the thin metal plate. Once the safety valve and thin metal plate have separated, the electrode is disconnected from the exterior can and current can no longer flow. Other safety devices in the battery 200 are a PTC device 260, and a gas release vent 288.

Figure 3:
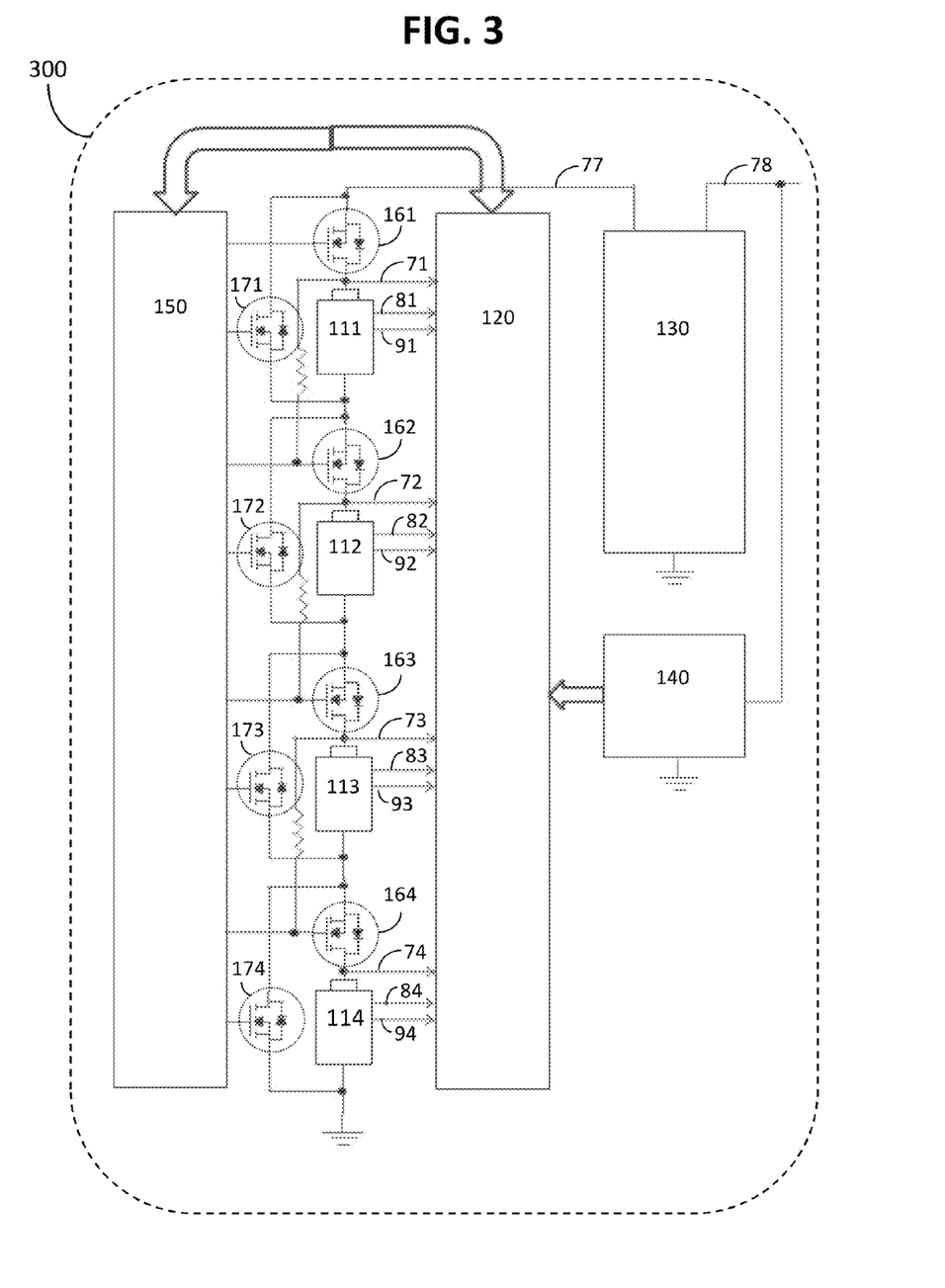
FIG. 3 shows a diagram of a battery system according to the invention.

FIG. 3 is a schematic diagram showing an embodiment of a battery system 300 capable of balancing voltages in response to a fault condition. The system 300 includes four lithium-ion cells 111-114 connected in series. In an embodiment, these can be the 18650 cylindrical-type cells with a nominal voltage of 3.7 V. Other embodiments may include different types of cells, or may include fewer than or more than four cells.

Embodiments of the battery 300 may include various cathodes, anodes, and electrolytes known in the art. For example, the cathode may comprise lithium cobalt oxide ($LiCoO_2$), lithium nickel manganese cobalt oxide ($Li[Ni_xMn_yCo_z]O_2$), lithium nickel cobalt aluminum oxide ($Li[Ni_xCo_yAl_z]O_2$), lithium iron phosphate ($LiFePO_4$), lithium manganese oxide ($LiMn_2O_4$), or any other material known in the art. The anode may be graphite or another suitable material. The electrolyte may comprise for example ethylene carbonate, dimethyl carbonate, diethyl carbonate, or a mixture thereof, along with a conducting lithium salt such as $LiPF_6$, $LiBF_4$, $LiAsF_6$, $LiCF_3SO_3$, or $LiClO_4$.

The battery-management system (BMS) 120, also known as a controller unit, receives voltage 71-74, temperature information 81-84, and resistance information 91-94 from each cell 111-114. The software of the BMS 120 can be configured to detect when one cell is getting too hot compared to the other cells. It can then respond by isolating the faulty cell from the others, rebalancing the voltages, or taking other steps to mitigate the situation before a thermal runaway or other problematic event can occur. The hardware of the BMS 120 may include thermal sensors, voltage sensors, current sensors, as well as electronic safety circuits that control the charging and discharging of the cells. The BMS 120 measures various cell parameters including current and voltage during operation and the software can determine the state of charge of the cells. In embodiments, the BMS 120 is configured to recognize when a parameter has reached a certain threshold indicative of a pre-fault condition, and respond by taking steps to prolong the operating life of the battery, while simultaneously notifying the user to find another power source.

The transistors can be metal-oxide-semiconductor field-effect transistors (MOSFETs) or any other transistor known in the art. The load switch or driver 150 is on the high side, meaning that it connects the cells to an electrical load, or disconnects them from it. It is coupled to a controller 120, which sends a signal to the high-side driver 150 based on inputs 71-74, 81-84, and 91-94, for example, from cells 111-114. If the controller 120 determines, for example, based on the inputs of cell 111 that there is a fault or there is a potential future fault, the controller signals the high-side driver to electronically isolate or turn off the defective cell 111 by turning off the N-channel MOSFET switch 161.

In one embodiment, the remaining cells 112-114 provide energy to an electronic device (not shown) such as a ventricular assist device (VAD) at the lower voltage that resulted from one cell being turned off. In such embodiments, the VAD would have been designed to accept the lower voltage for operation. Optionally, the system 300 comprises a DC/DC converter or voltage booster 130. If one or more cells are isolated by the BMS 120 due to faults or potential faults, the voltage booster 130 ramps up the voltage of the remaining cells to maintain a normal power level to the VAD or other device. The controller unit 120 performs cell voltage balancing to keep all the cells in a battery pack at close to the same voltage so as to avoid a destabilizing over-charge. In some embodiments this may be accomplished by using switching shunt resistors across the cell to bring high voltage cells into line with the other cells in the pack. The output voltage is maintained at a level required by the boost converter 130, as long as one or more cells are active. This redundant cell design allows the battery to maintain its normal output level in a fault situation. In some embodiments the battery is designed to be able to continue functioning with one or more cells turned off. In other embodiments the battery can continue functioning for only a short time with one or more cells turned off.

In another embodiment of battery system 300, one of the cells is a reserve cell, which can be connected via a shunt (not shown). The reserve cell can be a backup or spare cell, which is not in use during regular operation of the battery. Alternatively, the reserve cell can have a regular function of powering auxiliary electronics of the VAD or other device. When one of the cells 111-114 fails and has been isolated by the operation described above, the reserve cell is switched on and brought into the series by activating the shunt. In embodiments where the reserve cell's normal function is to provide auxiliary power, the controller 120 assesses the failed or isolated cell to determine whether it is still capable of powering the auxiliary electronics. If it is, the controller 120 proceeds to switch that cell and the reserve cell, so that the reserve cell comes into series with the other active cells to provide power to the device, and the failed cell provides power to the auxiliary electronics. If the failed cell is incapable of powering even the less demanding auxiliary electronics, it remains isolated and the pack of functioning cells is used to power the device and the auxiliary electronics.

In some embodiments the controller 120 can attempt to revive a failed cell by charging it, via slow charge, pulse charge, or another type of charge known in the art. For implantable electronic devices, the type of charge should be compatible with use inside the body. For example, fast charging that results in excessive temperature increase may not be desirable in some embodiments. In embodiments where the cell has not yet failed, but has been determined to be in a pre-failure condition, that pre-failure cell may be revived by the controller 120 in the same manner as described above.

The present disclosure also provides an alert system for notifying the user when a battery fault has occurred or will potentially occur. Systems of the invention provide differentiable alerts for faults or potential faults of different severity. For example, a small or insignificant fault may trigger a minor alert to keep the user apprised of the battery's condition, whereas a more severe fault may trigger a more emphatic or even painful alert, such as a shock, that underscores the gravity of the fault. Alerts can correspond to potential faults of varying degrees as well.

Figure 4:
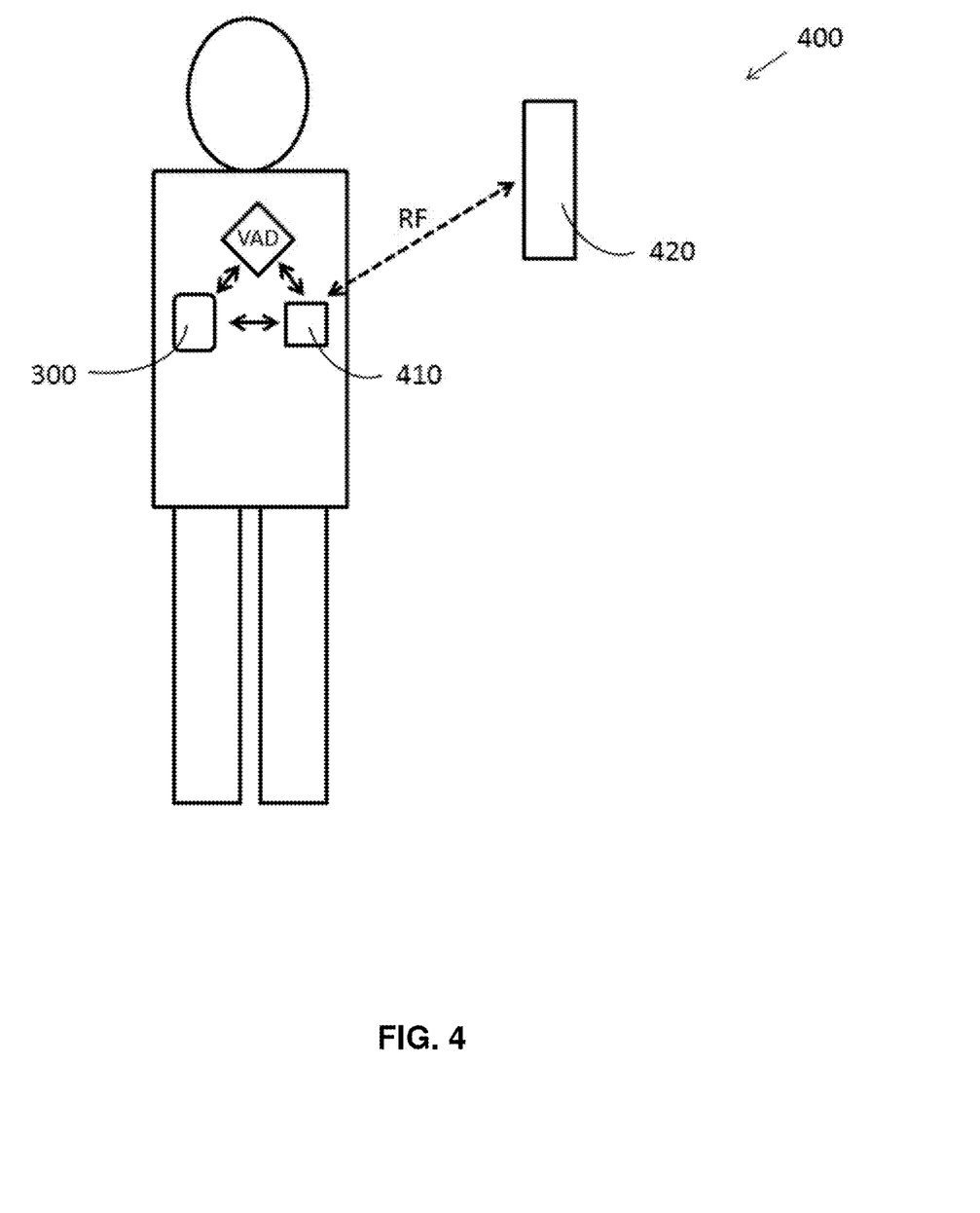
FIG. 4 shows a system for alerting a user to a battery fault using a radio-frequency signal.

FIG. 4 depicts an embodiment of an alert system 400 for alerting a user to an error or a potential error in an implanted battery connected to an implantable electronic device such as a VAD. The error can be a battery fault or another error in the device, or it may be a condition that the BMS has determined is a likely precursor to a fault or other error. The VAD is in electrical communication with a battery system 300 and with an internal controller 410 that is implanted in the user's body. An external controller 420 can be situated outside the user's body. The external controller 420 is capable of receiving radio frequencies from the internal controller 410. In the event of a minor fault or potential fault in the battery 300, a signal is sent to the external controller 420. The external controller 420 may activate a sound, a vibration, or any other indication that can be perceived by the user. In the event of a minor fault where the battery 300 is still functional, the internal device is capable of sending the RF signal. Therefore, this system is ideal for reporting minor faults, potential future faults, or any fault that does not cause the device to shut down completely. Upon perceiving the alert, the user may take an action such as recharging the battery or scheduling a surgery to replace the battery.

More severe faults or potential faults may have a different type of alert. The differentiation between minor and major faults or potential faults helps the user determine what response, if any, is needed. Also, if the condition constitutes a life-threatening emergency, the alert should be comparably acute. For severe errors, the alert should be sufficient to wake the user if necessary.

Figure 5:
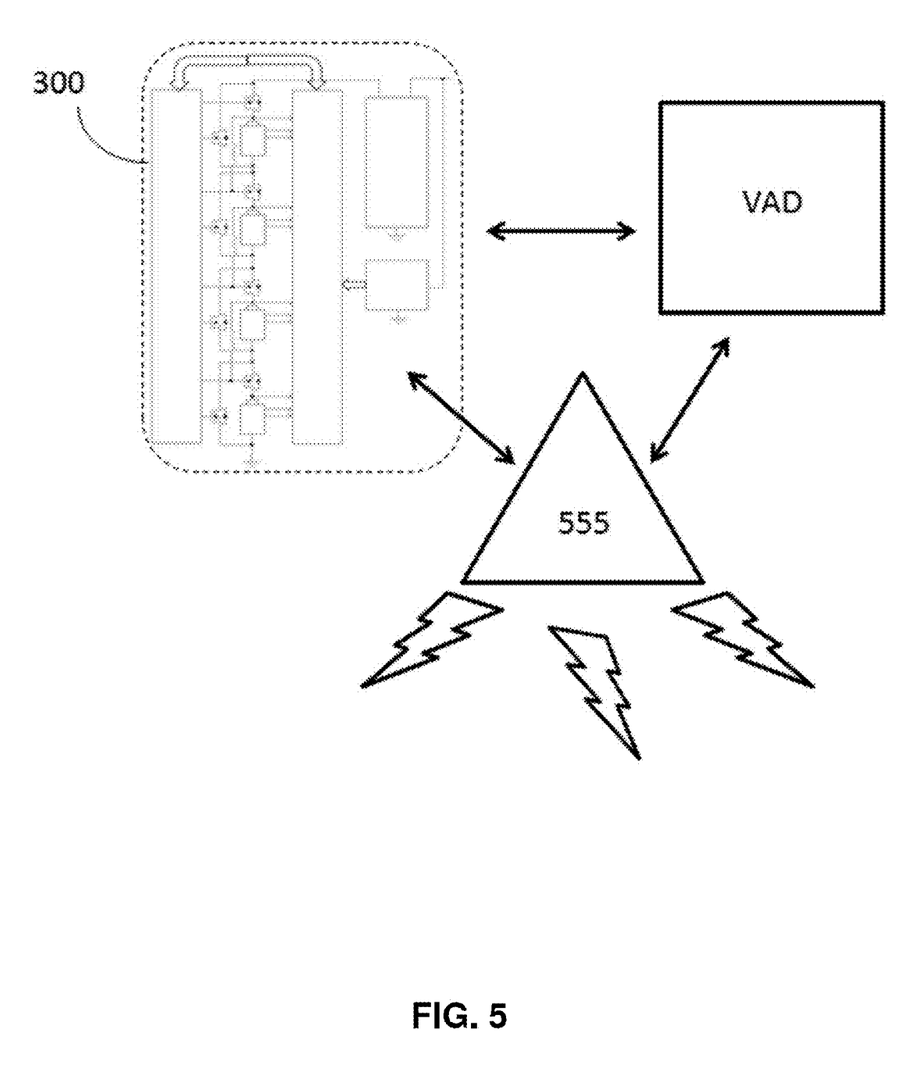
FIG. 5 shows a system for alerting a user to a battery fault including a capacitor.

The present disclosure provides an elevated alert for more serious faults and potential faults. The alert can be a strong vibration, an electrical shock, or another jarring sensation to the user. FIG. 5 depicts a system 500 with a configuration including a battery 300, a VAD, and a separate power source 555. In the event that the battery 300 fails completely and is no longer capable of providing power at all, the separate power source 555 is activated to produce an alert. The power source 555 can be a capacitor compatible with medical implants, such as the KEMET C2220X104K2RACTU capacitor available from Newark Corporation (Chicago, Ill.). An important safety feature of the disclosure is that in the event of a major error or fault in an implantable electronic device, an alert can still be sent, owing to the separate and independent power source 555.

The alarm generated by the power source 555 can be triggered by the power level of the battery falling below a threshold. The threshold can be measured using a comparator. If the battery level drops to the predetermined threshold, the capacitor triggers an electrical shock to notify the user. In another embodiment, the capacitor activates an internal vibration that can be felt by the user. The system may have a variety of alerts, each corresponding to a different type or level of fault.

Figure 6:
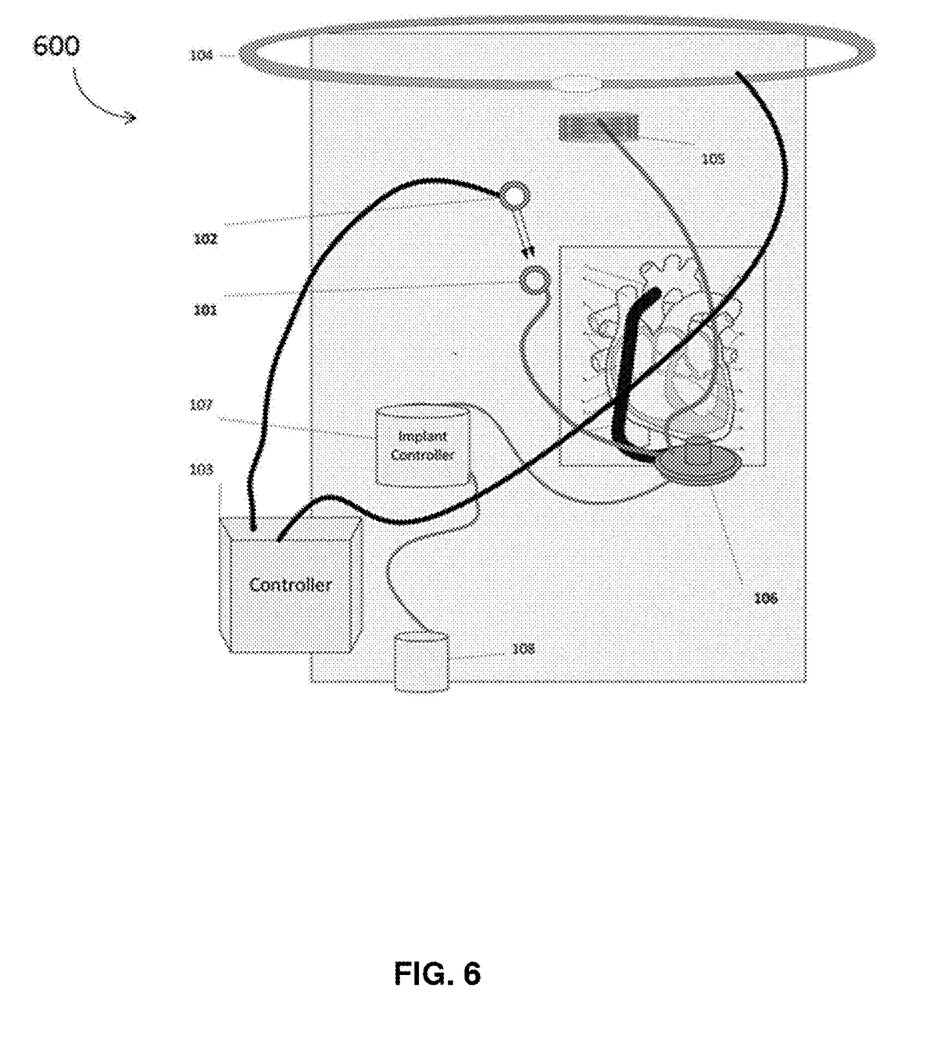
FIG. 6 shows a backup power system.

In the event of a severe or catastrophic fault wherein the user must immediately seek backup power for the device, the system can include external wired or wireless power source. Examples of backup power sources can be found in U.S. Patent Publication 2013/0053624, filed Aug. 22, 2012, the contents of which are incorporated herein in their entirety. FIG. 6 depicts a power transfer system 600 that can be used with the present disclosure as a backup power source. The system 600 includes a power transfer belt 104 connected to an external controller 103, which provides power to the power transfer belt 104. The wireless backup power source can be a wearable device such as a belt or a transfer vest, or it may constitute any other suitable configuration. As shown, the power transfer belt 104 can provide wireless power transfer to the internal power receiver 105, which is connected to an implanted electronic device 106.

The system may also comprise a wired external power source, which can be separate from or connected to the wireless power source. In FIG. 6, the external power transfer system 600 comprises an external male unit 102 with prongs, which can be inserted through the skin and coupled to an implanted female unit 101. The male unit 102 is connected to the controller 103, and the female unit is connected to the implanted device 106. Thus, the connection between the male unit 102 and female unit 101 creates a wired connection between the implanted device 106 and the controller 103, which provides power. The external power source may have a feature that communicates to the internal battery to shut off in the event that the internal battery is continuing to function.

In some embodiments, both a wireless and a wired external power source are provided for backup power. In other embodiments, only one or the other is provided. In some embodiments, the wireless external power source is a primary backup power source, and the wired external power source is a secondary backup power source for when the primary backup fails.

In addition to monitoring battery conditions and alerting the user, the present disclosure provides additional safety features that can be used in conjunction with or separately from the safety features described above. FIGS. 7-13 depict various embodiments of improved battery casings for implantable LIBs. Unlike known implantable batteries, which exclude vents due to the potential bodily harm that could result from venting within the body, the present disclosure reveals designs for battery casings that allow venting to safely occur. These casings prevent explosion or other problems associated with increased pressure in a battery, while minimizing risk to the user.

Figure 7:
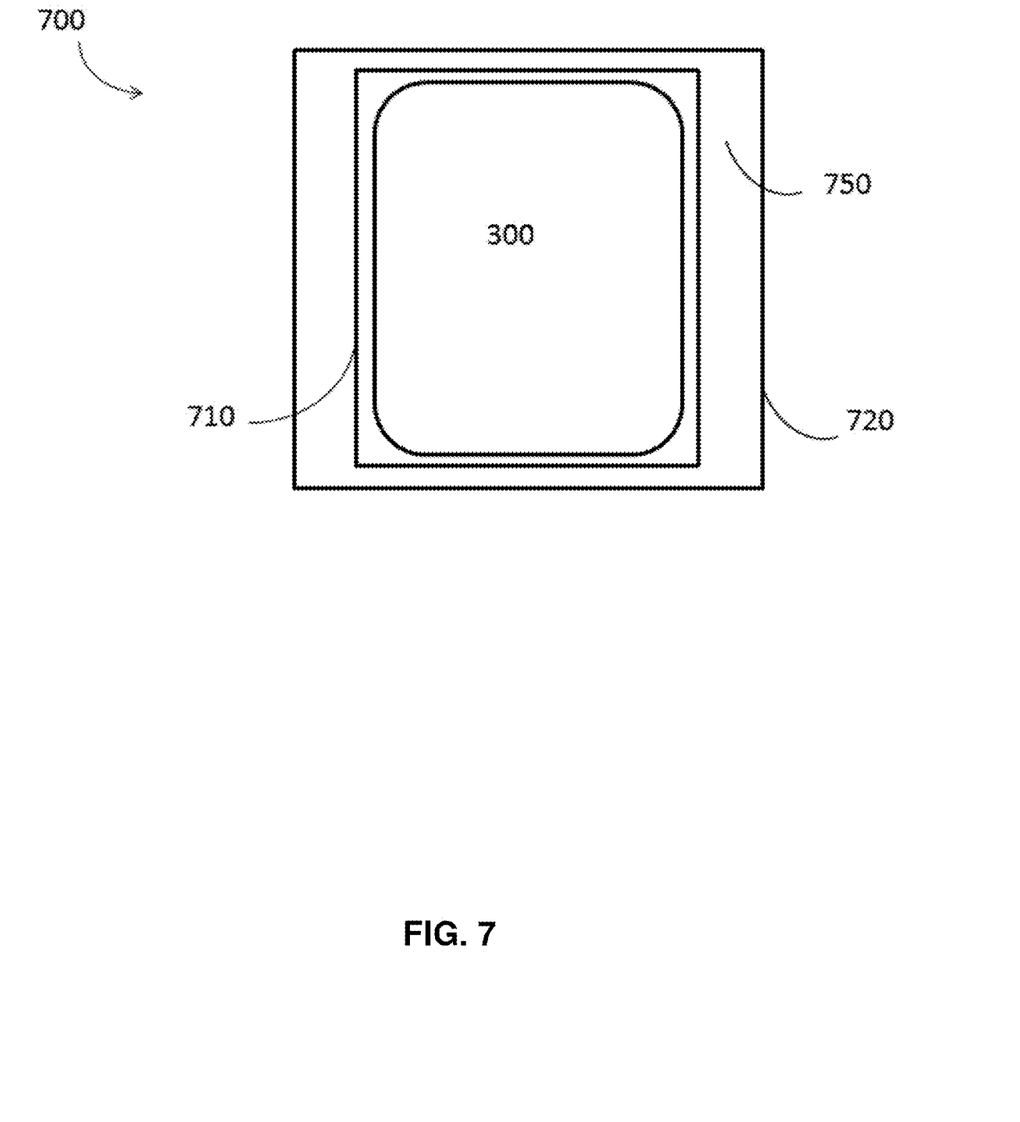
FIG. 7 shows a double-walled battery casing.

FIG. 7 shows a schematic view of a device 700 including a double-walled battery casing. The battery 300 is surrounded by an inner wall 710, which is situated within an outer wall 720. There is a vacuum 750 in between. The walls 710 and 720 can be made from aluminum, steel, stainless steel, titanium, titanium alloy, or any other suitable material known in the art. The double-walled design provides added protection against pressures that build up inside the battery unit 300 when cells vent.

The vacuum 750 has a stabilizing effect on the temperature of the battery. In a normal implanted battery pressure may increase as temperatures rise. However, the vacuum 750 surrounding the battery 300 mitigates the pressure increase that would otherwise result from the hot vapors. The vacuum 750 insulates the battery from the outside, preventing an increased temperature in a fault situation from causing discomfort or burns. It also can allow the cells to maintain a temperature below body temperature, so that the battery does not necessarily have to be configured to operate at about 37° C. Additionally, the battery experiences less of a temperature rise on charging, making it more efficient and allowing for fast charging. In embodiments that include a PTC device, the vacuum 750 makes PTC device less likely to activate, thereby prolonging the life of the cell.

Figure 8:
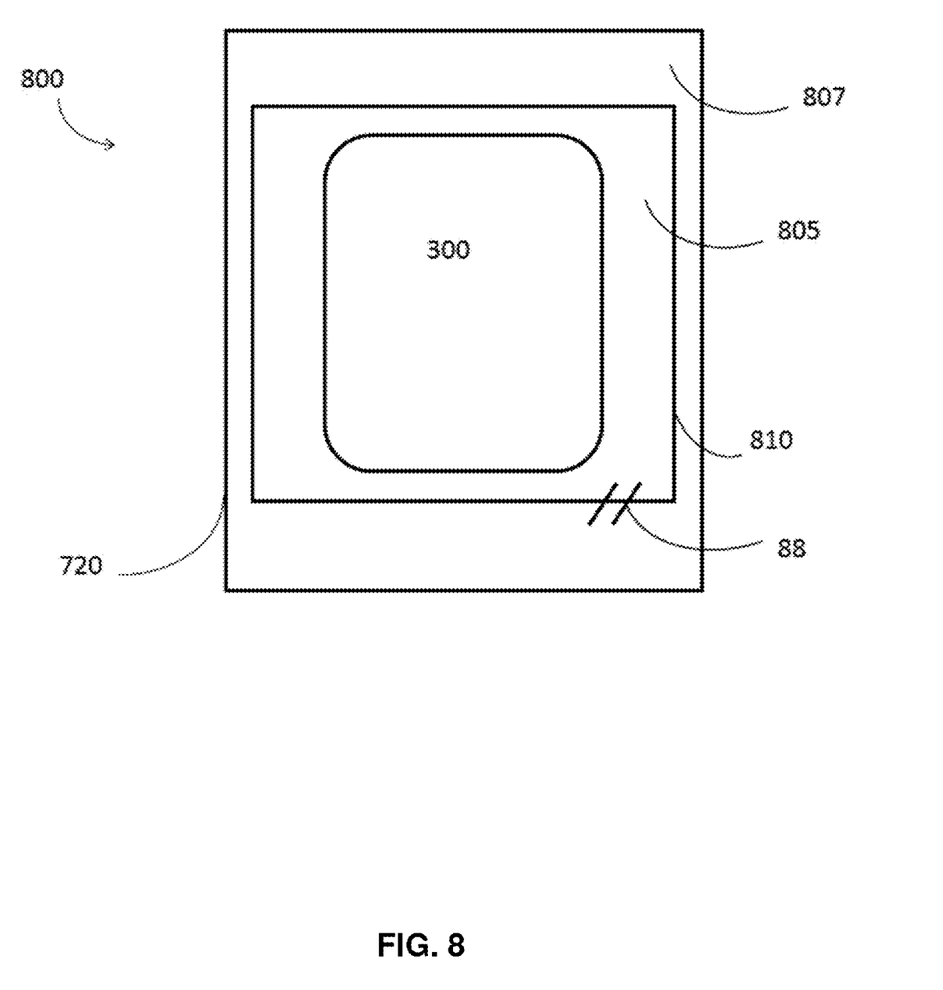
FIG. 8 shows a battery casing with a dividing wall and a vent.

In an embodiment of the casing depicted in FIG. 8, the controller case is divided into two sections by a dividing wall 810, and the dividing wall 810 has its own vent 88. The first section 805 is defined by the dividing wall 810. The second section 807 is a reservoir for the vent pressure. When a cell or cells vent, and the pressure increases inside the first section 805, the danger of the case bursting and releasing organic solvent into the body is minimized because the vent 88 in the dividing wall 810 will open and release the vapors into the second section 807.

Figure 9:
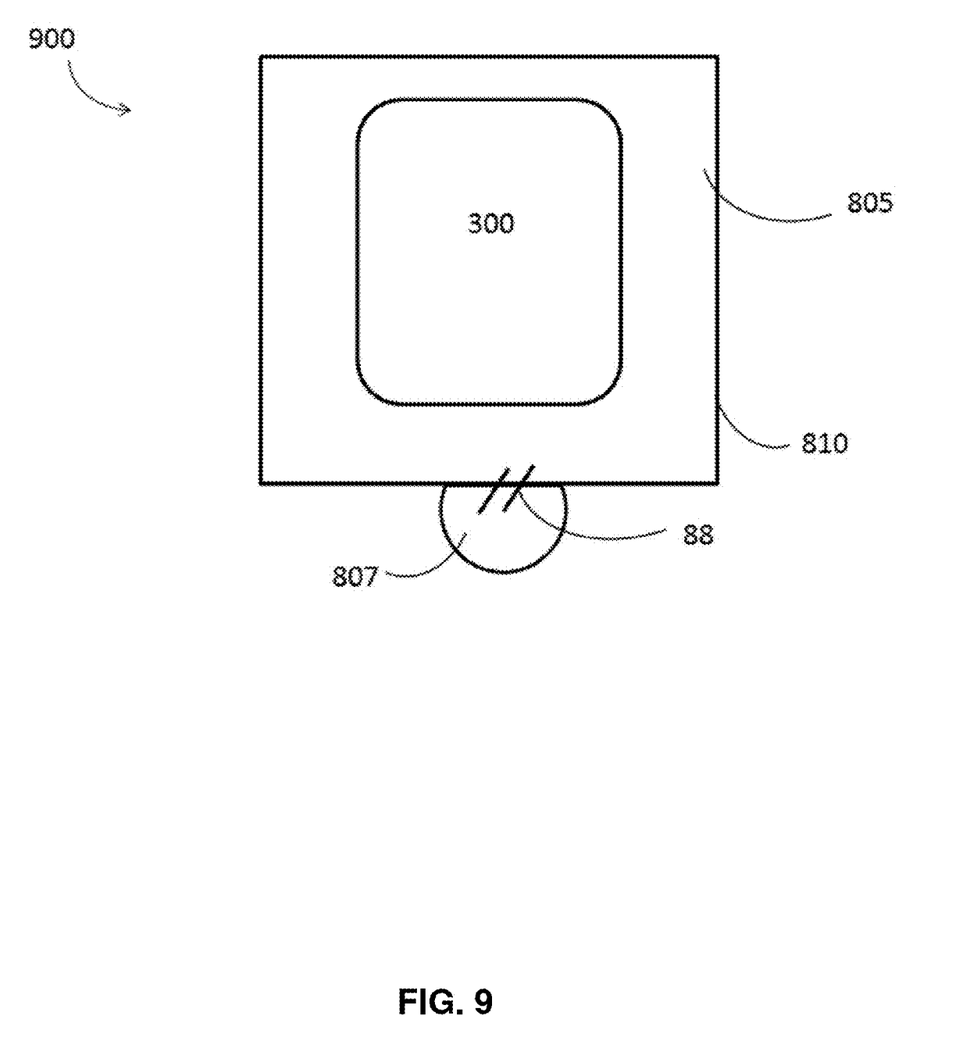
FIG. 9 shows a battery casing with a reservoir section.

FIG. 9 shows another embodiment capable of mitigating extreme pressure differences by directing the first section vent into reservoir section 907 that is an inflatable high volume balloon. When pressure inside the first section 805 increases, the vent 88 may open, releasing organic solvents into the inflatable reservoir section 907. Because the reservoir section 907 is also deflatable, it may reduce in size as the released vapors eventually cool.

Figure 10:
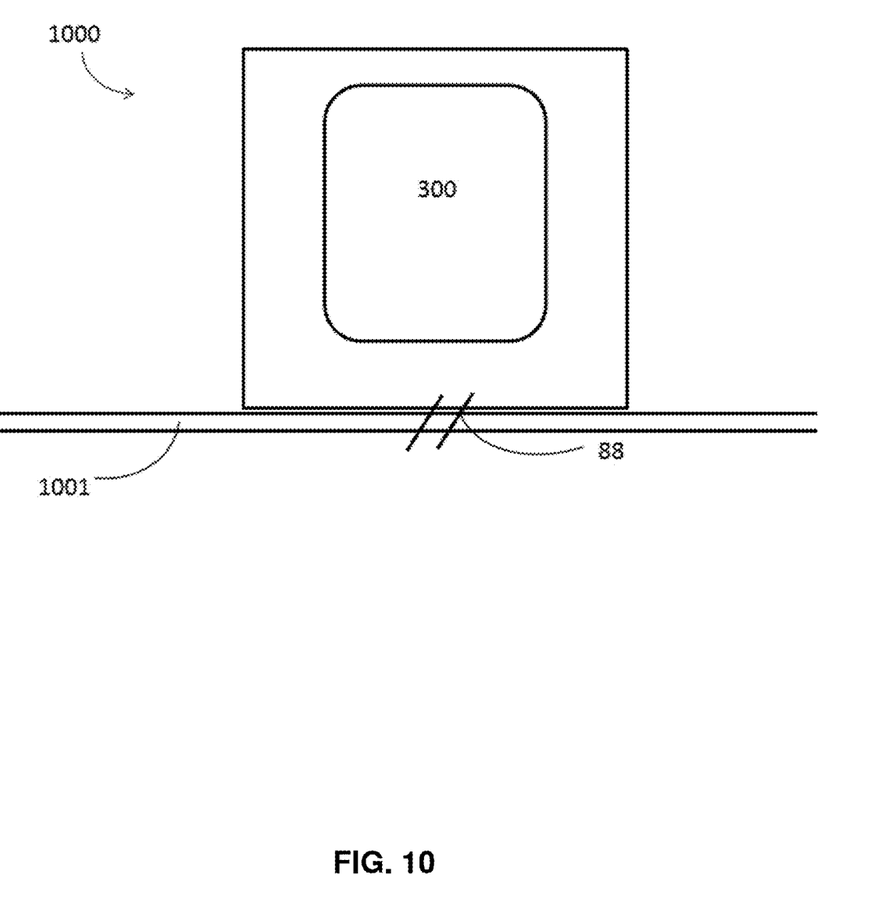
FIG. 10 shows a battery casing with a vent capable of directing vapors outside the body.

FIG. 10 shows a controller casing 1000 including a vent 88 that directs vapors to the outside of the body. In the configuration depicted in FIG. 10, the casing is implanted near an external surface 1001 of the body. This embodiment may be considered a last-resort for relieving a faulty battery from pressure buildup. The vent 88 is configured to break through the skin and release the pressure outside the body.

In extreme situations, it is dramatically better to direct the damage to the skin rather than to internal organs.

Figure 11:
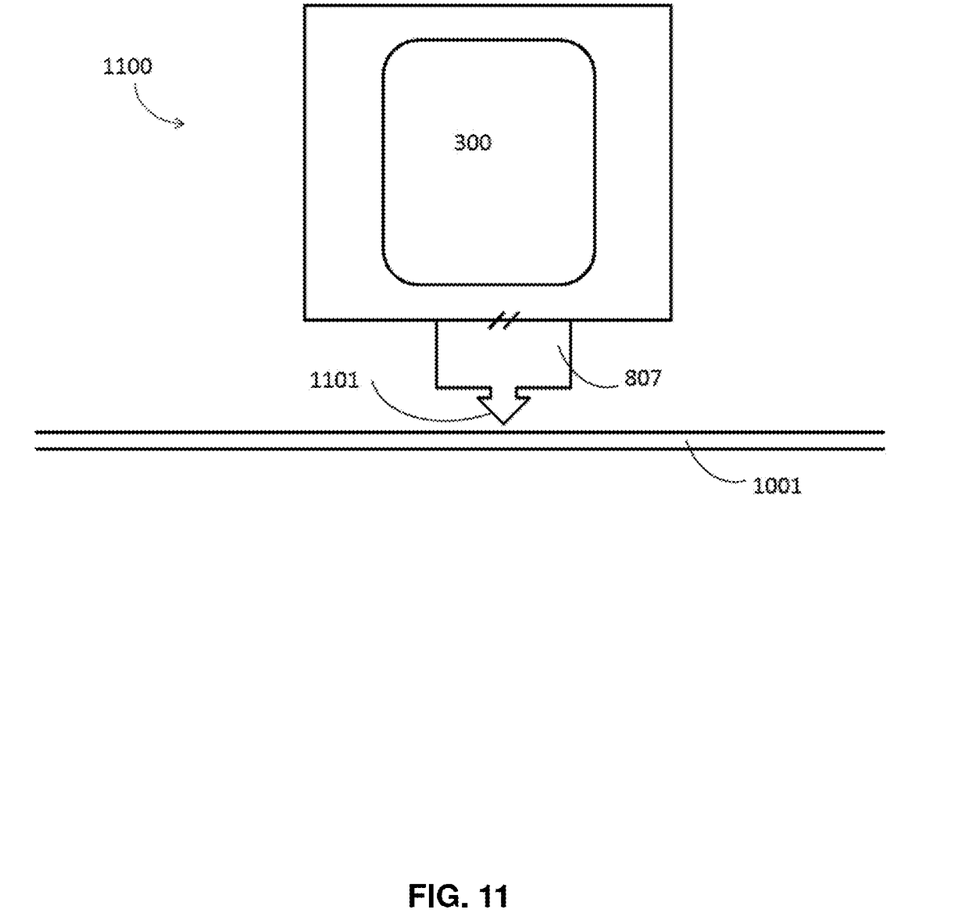
FIG. 11 shows a battery casing with a reservoir section that includes a sharp header.

FIG. 11 shows an embodiment wherein the inflatable reservoir section 807 comprises a sharp or arrow-like header 1101 that is positioned to break the surface of the skin and release pressure outside the body. The section 807 may be configured to break open to release organic solvents once it has broken through to the outside of the body.

In another embodiment, the battery is located within a flexible casing envelope. When vapors are vented, they collect in the envelope. The envelope prevents harmful vapors or liquids from coming into contact with the body. The electronic circuitry in the control unit, whether located in the same section as the battery pack, or in the second section, can be encased in a polymer or other material to isolate it and prevent it from being damaged by any organic solvent vapors or liquids that are vented by the cells.

In other embodiments, insulating materials can be used to protect parts of the battery. Thermal insulation can be inserted between cells to thermally isolate them from each other. The cells can also simply be physically separated by air or a vacuum to prevent direct conduction of heat between them. In other embodiments, cells are divided by insulating plates comprising foam, ceramic, carbon composites, silica fiber tiles, glass fiber insulation, or the like.

In other embodiments, a heat pipe or heat pin can be used to cool the batteries. The heat pipe controls the transfer of heat between surfaces using thermal conductivity. It can be filled with a solvent whose boiling point is slightly greater than body temperature like cyclopentane (49° C.), dichloromethane (40° C.), acetone (56° C.), or methylene chloride (40° C.).

In other embodiments, an absorbing material can be included in the control unit to absorb any leaked or vented organic solvent. Without implying any limitation, absorbing materials may comprise vermiculite in granular or other form, absorbing paper (non-woven or woven) or fibers, sawdust, and the like.

What is claimed is:

1. A method for mitigating a battery condition in an implanted multi-cell battery pack, the method comprising:
   identifying a parameter of a cell that has exceeded a threshold;
   determining based on the parameter that the cell has a condition;
   isolating the cell having the condition from one or more other cells; and
   providing backup power to mitigate a loss of voltage from the isolated cell.

2. The method of claim 1, wherein the parameter is a probability of explosion.

3. The method of claim 1, wherein the condition is a fault.

4. The method of claim 1, wherein the condition is indicative of a future fault.

5. The method of claim 1, wherein providing backup power comprises boosting the voltage of the one or more non-isolated cells.

6. The method of claim 5, wherein the voltage is boosted with a DC/DC converter.

7. The method of claim 1, wherein providing backup power comprises connecting a reserve cell to the one or more non-isolated cells to substitute for the loss of voltage from the isolated cell.

8. The method of claim 7, wherein the reserve cell is a spare cell.

9. The method of claim 7, wherein the reserve cell is a cell for providing energy to auxiliary electronics.

10. The method of claim 9, further comprising determining if the isolated cell is capable of providing energy to the auxiliary electronics.

11. The method of claim 7, wherein the reserve cell is connected to the one or more non-isolated cells by an electronic shunt.

12. The method of claim 7, further comprising the step of reviving the isolated cell.

13. The method of claim 12, wherein reviving the isolated cell comprises providing a slow charge or a pulse charge to the isolated cell.

14. The method of claim 1, wherein the parameter is temperature, pressure, or impedance.

15. The method of claim 1, wherein the steps are performed by a battery management system.

16. The method of claim 1, wherein the battery pack comprises four lithium-ion cells.

17. The method of claim 1, wherein the cells are connected in series.

18. A system for powering an electronic device, the system comprising:
   a battery pack comprising a plurality of cells;
   a battery management system configured to:
     identify a parameter of one of the plurality of cells that has exceeded a threshold;
     determine based on the parameter that the cell has a condition;
     isolate the cell having the condition from one or more other cells; and
     provide backup power to mitigate a loss of voltage from the isolated cell.

19. The system of claim 18, wherein the parameter is a probability of explosion.

20. The system of claim 18, wherein the condition is a fault.

21. The system of claim 18, wherein the condition is indicative of a future fault.

22. The system of claim 18, further comprising a boost converter.

23. The system of claim 22, wherein the battery management system is configured to provide backup power by causing the boost converter to increase the voltage of the one or more non-isolated cells.

24. The system of claim 18, further comprising a reserve cell connected to the battery pack by a shunt.

25. The system of claim 24, wherein the battery management system is configured to provide backup power by connecting the reserve cell to the one or more non-isolated cells by activating the shunt.

26. The system of claim 18, wherein the cells are lithium-ion cells.

27. The system of claim 18, wherein the boost converter is a DC/DC converter.

28. The system of claim 18, wherein the electronic device is a ventricular assist device.

29. The system of claim 18, wherein each of the plurality of cells is connected in series.

30. The system of claim 18, wherein the plurality of cells comprises four lithium-ion cells.

31. The system of claim 18, wherein the battery management system is further configured to revive the isolated cell.

32. The system of claim 31, wherein reviving the isolated cell comprises providing a slow charge or a pulse charge to the isolated cell.

33. The system of claim 18, further comprising a backup power source configured to provide power in the event that the plurality of cells fails.

34. A system for alerting a user to a condition of an electronic device, the system comprising:
   a battery pack connected to an implanted electronic device; and
   a battery management system connected to the battery pack configured to:
      identify a parameter of a cell in the battery pack that has exceeded a threshold;
      determine based on the parameter that the cell has a condition; and
      trigger an alert.

35. The system of claim 34, wherein the parameter is a probability of explosion.

36. The system of claim 34, wherein the condition is a fault.

37. The system of claim 34, wherein the condition is indicative of a future fault.

38. The system of claim 34, further comprising a radio transmitter configured to send a radio frequency signal to an external receiver, and wherein the alert comprises the radio frequency signal.

39. The system of claim 34, further comprising a vibration device configured to vibrate, and wherein the alert comprises a vibration.

40. The system of claim 34, further comprising a shock generator connected to a separate power source, configured to generate an electric shock, and wherein the alert comprises the electric shock.

41. The system of claim 40, wherein the separate power source is a capacitor.

42. The system of claim 34, wherein the implantable medical device is a ventricular assist device.

43. The system of claim 34, further comprising an external power source capable of providing power to the implanted electronic device.

44. The system of claim 43, wherein the external power source is a wireless power transfer belt.

45. The system of claim 43, wherein the external power source is electrically coupled to an external male unit comprising one or more prongs configured to be inserted through the epidermis of the user and received by an internal receiving port connected to the implanted electronic device.

* * * * *